United States Patent [19]

Barbera et al.

[11] Patent Number: 4,978,522
[45] Date of Patent: Dec. 18, 1990

[54] ORAL COMPOSITIONS

[75] Inventors: Melvin A. Barbera; Francis O. Agricola, both of Cincinnati; Robert V. Faller, Amelia; Worth D. Bowman, West Chester, all of Ohio

[73] Assignee: The Procter & Gamble Company, Cincinati, Ohio

[21] Appl. No.: 320,893

[22] Filed: Mar. 9, 1989

Related U.S. Application Data

[63] Continuation of Ser. No. 106,479, Oct. 6, 1987, abandoned, and a continuation of Ser. No. 828,110, Feb. 10, 1986, abandoned.

[51] Int. Cl.$^5$ ............................ A61K 7/18; A61K 7/22
[52] U.S. Cl. .......................................... 424/52; 424/49; 424/464; 514/835; 514/901
[58] Field of Search ..................... 424/48, 49, 52, 464; 514/835, 901

[56] References Cited

U.S. PATENT DOCUMENTS

| | | | |
|---|---|---|---|
| 4,224,310 | 9/1980 | Shah | 424/49 |
| 4,367,219 | 1/1983 | Schole | 424/49 |
| 4,415,549 | 11/1983 | Shah | 424/49 |

FOREIGN PATENT DOCUMENTS 0079611  5/1983  European Pat. Off. .

OTHER PUBLICATIONS

Zero, *Journal of Dental Research*, 61(3), 451–455 (1982).
Featherstone, *Journal of Dental Research*, 62(10), 1049–1053 (1983).
Featherstone, *Demineralization and Remineralization of the Teeth*, IRL, Press Limited, Oxford, England, 1983, pp. 89–109.

*Primary Examiner*—Ronald W. Griffin
*Attorney, Agent, or Firm*—Douglas C. Mohl; Kim William Zerby; Jack D. Schaeffer

[57] ABSTRACT

Oral compositions effective against caries containing strontium EDTA and a soluble fluoride ion source are described herein.

4 Claims, No Drawings

ORAL COMPOSITIONS

This is a continuation of application Ser. No. 106,479, filed on Oct. 6, 1987 now abandoned and a continuation of application Ser. No. 828,110 filed on Feb. 10, 1986, now abandoned.

TECHNICAL FIELD

The present invention relates to oral compositions such as liquid dentifrices, toothpastes and mouthwashes, which provide an anticaries benefit.

BACKGROUND OF THE INVENTION

The role of fluoride in the remineralization of carious lesions is well known. The use of agents to enhance this benefit is also well known. One such agent is strontium.

While strontium's inclusion in oral compositions containing fluoride is desirable the agents form an insoluble precipitate unless separated before use or the strontium ions are complexed so as not to be available to form the precipitate. Strontium complexed with ethylene diaminetetraacetic acid (EDTA) is such a complex.

The effect of a strontium-EDTA complex in combination with sodium recinoleate and a fluoride source is found in the *Journal of Dental Research* (1982) 61 (3) 451–455. The combined effect of strontium and fluoride in reducing the acid solubility of enamel is also disclosed in the *Journal of Dental Research* (1983) 62 (10) 1049–1053. A further reference discussing the effect of strontium and fluoride is Featherstone, J.D.B. "Remineralization of Artificial Carious Lesions In-vivo and In-vitro", *Proceedings Workshop* (1983) IRL Press Ltd.

The use of strontium in combination with fluoride in oral compositions is also disclosed in a number of patent references. Included among these references are U.S. Pat. No. 3,888,976, June 10, 1975 to Mlkvys disclosing an effervescent mouthwash tablet containing strontium ions and possibly a fluoride ion source. U.S. Pat. No. 4,367,219, Jan. 4, 1983 to Schole discloses dentifrices containing a combination of strontium EDTA, a recinoleate salt and a fluoride ion source. U.S. Pat. No. 4,415,549, Nov. 15, 1983 to Shah et al. discloses toothpastes containing a glycyrrhizinate salt, strontium EDTA and a fluoride ion source. Finally European patent application no. 0.079,611, June 6, 1983, Shah, discloses oral compositions containing a strontium EDTA complex and a fluoride ion source.

Although the prior art discloses complexes of strontium and EDTA, there is still the need for improvements particularly in achieving greater strontium efficiency.

It has been surprisingly found by the present inventors that very low strontium concentrations can provide enhanced fluoride uptake of a degree not predictable by the prior art.

It is an object of the present invention, therefore, to provide compositions having effectiveness against caries using low levels of strontium.

It is a further object of the present invention to provide compositions effective against caries utilizing strontium EDTA as the strontium ion source.

It is still a further object of the present invention to provide an effective method for providing caries protection.

These and other objects will become readily apparent from the detailed description which follows.

All percentages and ratios used herein are by weight unless otherwise specified.

SUMMARY OF THE INVENTION

The present invention embraces oral compositions comprising:

(a) a safe and effective amount of a strontium EDTA complex;

(b) a safe and effective amount of a soluble fluoride ion source; and (c) a pharmaceutically acceptable carrier.

The present invention also encompasses a method for increasing the amount of fluoride taken up by dental enamel.

DETAILED DESCRIPTION OF THE INVENTION

The compositions of the present invention comprise a strontium EDTA complex, a soluble fluoride ion source and pharmaceutically acceptable carrier.

By "oral compositions" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "carrier", as used herein, is meant a suitable vehicle which is pharmaceutically acceptable and can be used to apply the present compositions in the oral cavity.

Strontium EDTA

The strontium-EDTA complex used in the present invention can be formed by reacting disodium EDTA with a soluble strontium salt (e.g., strontium chloride). Similarly the complex can be formed using the complex described in U.S. Pat. No. 4,224,310, Sept. 23, 1980 to Shah, incorporated herein by reference. The EDTA:$Sr^{++}$ molar ratio is 1:1 so that no uncomplexed strontium ions will be available when the complex is put into the carrier along with the soluble fluoride ion source. The strontium EDTA complex is used in the present compositions to provide a strontium ion concentration of from about 2 to about 10,000, preferably from about 5 to about 5,000, more preferably from about 500 to about 4400 ppm at 25° C. in the composition or when it is used.

Fluoride Ion Source

The water-soluble fluoride compound is present in the compositions of this invention in an amount sufficient to give a fluoride ion concentration of from about 0.0025% to about 5.0% by weight, preferably from about 0.005% to about 2.0% by weight at 25° C., to provide anticaries effectiveness. Preferred fluorides are sodium fluoride, stannous fluoride, indium fluoride, and sodium monofluorophosphate. U.S. Pat. No. 2,946,735, July 26, 1960 to Norris et al. and U.S. Pat. No. 3,678,154, July 18, 1972 to Widder et al. disclose such salts as well as others. These references are incorporated herein by reference.

Pharmaceutically Acceptable Carrier

The carrier for the components of the present invention can be any vehicle suitable for use in the oral cavity. Such carriers include the usual components of mouthwashes, toothpastes, toothpowders, prophylaxis pastes, lozenges, gums and the like and are more fully described hereinafter. Dentifrices and mouthwashes are the preferred systems with toothpastes being the more preferred.

Toothpastes contain as a major component an abrasive. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, June 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasive are described in U.S. Pat. No. 4,340,583, July 29, 1982, incorporated herein by reference.

The abrasive in the dentifrice compositions described herein is present at a level of from about 6% to about 70%, preferably from about 15% to about 25% when the dentifrice is a toothpaste. Higher levels, as high as 90%, may be used if the composition is a toothpowder.

Flavoring agents can also be added to the dentifrice and other compositions of the present invention. Suitable flavoring agents include oil of wintergreen, oil of peppermint, oil of spearmint, oil of sassafras, and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight.

The compositions of this invention also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al. in U.S. Pat. No. 4,051,234, Sept. 27, 1977 incorporated herein by reference.

Water is also present in the compositions of this invention. Water employed in the preparation of commercially suitable compositions should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can also be used as part of the thickening agent to further improve texture. Thickening agents in an amount from 0.5% to 5.0% by weight of the total composition may be used.

It is also desirable to include a humectant in a toothpaste to keep it from hardening. Suitable humectants include glycerin, sorbitol, and other edible polyhydric alcohols at a level of from about 10% to about 70%.

Another preferred embodiment of the present invention is a mouthwash composition. Conventional mouthwash composition components can comprise the carrier for the actives of the present invention. Mouthwashes generally comprise from about 20:1 to about 2:1 of a water/ethyl alcohol solution and preferably other ingredients such as flavor, sweeteners, humectants and sudsing agents such as those described above. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably from 0.03% to 0.3%) flavoring agent, and the balance water.

Suitable lozenge and chewing gum components are disclosed in U.S. Pat. No. 4,083,955, Apr. 11, 1978 to Grabenstetter et al., incorporated herein by reference.

The pH of the present compositions and/or its pH in the mouth can be any pH which is safe for the mouth's hard and soft tissues. Such pH's are generally from about 3 to about 10, preferably from about 4 to about 8. The present compositions, since they are designed to deliver fluoride to tooth enamel, should not contain materials which would cause significant loss of strontium and/or fluoride ions.

METHOD OF MANUFACTURE

The carrier compositions of the present invention can be made using methods which are common in the oral products area. A specific method of manufacture is set forth in the Examples.

COMPOSITION USE

The present invention in its method aspect involves applying to the oral cavity safe and effective amounts of the compositions described herein. These amounts (e.g. from about 0.3 to about 15 g), if it is a toothpaste or mouthwash, are kept in the mouth for from about 15 to about 30 seconds.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLE I

The composition given below is exemplary of the present invention.

| Component | Weight % |
| --- | --- |
| $Na_2$ EDTA $2H_2O$ | 0.935 |
| Strontium Chloride $6H_2O$ | 0.667 |
| Sodium Fluoride | 0.243 |
| Silica Dental Abrasive[1] | 20.000 |
| Sodium Saccharin | 0.130 |
| Titanium Dioxide | 0.700 |
| Flavor | 0.600 |
| Carboxymethylcellulose | 0.600 |
| Tween 80[2] | 0.900 |
| Dye | 0.050 |
| Water | 19.000 |
| Sorbitol (70% Aqueous Solution) | q.s. 100% |

[1]Precipitated silica identified as Zeodent 119 offered by J. M. Huber
[2]POE (20) sorbitan monooleate offered by ICI Americas Inc.

The above composition is prepared by putting 50% of the sorbitol into a main mix tank containing all of EDTA, adding 50% of the water and mixing for a few minutes. Strontium chloride is then dissolved in 10% of the water and added to the main mix tank. The desired pH is then obtained by immediately adding HCl or NaOH. Next sodium fluoride is dissolved in the remaining water and added to the main mix tank, followed by the silica abrasive, sodium saccharin, titanium dioxide and flavor. In a separate tank, the binder is mixed with the remaining sorbitol and added to the main mix tank followed by the surfactant and the dye. The final mixture is heated to 70° C. processed through a mill and deaerated if necessary.

EXAMPLE II

Given below is another composition representative of the present invention.

| Component | Weight % |
| --- | --- |
| $Na_2$ EDTA $2H_2O$ | 0.467 |
| Strontium Chloride $6H_2O$ | 0.333 |
| Sodium Fluoride | 0.111 |
| Silica Dental Abrasive[1] | 20.000 |
| Sodium Saccharin | 0.130 |
| Titanium Dioxide | 0.700 |
| Flavor | 0.600 |
| Carboxymethylcellulose | 0.600 |
| Sodium Alkyl Sulfate | 2.500 |
| Dye | 0.050 |
| Water | 19.000 |
| Sorbitol (70% Aqueous Solution) | q.s. 100% |

[1]Precipitated silica identified as Zeodent 119 offered by J. M. Huber

EXAMPLE III

Given below is yet another composition representative of the present invention.

| Component | Weight % |
| --- | --- |
| $Na_2$ EDTA $2H_2O$ | 0.140 |
| Strontium Chloride $6H_2O$ | 0.100 |
| Sodium Fluoride | 0.243 |
| Silica Dental Abrasive[1] | 20.000 |
| Sodium Saccharin | 0.130 |
| Titanium Dioxide | 0.700 |
| Flavor | 0.600 |
| Carboxymethylcellulose | 0.600 |
| Sodium Alkyl Sulfate | 2.000 |
| Dye | 0.050 |
| Water | 19.000 |
| Sorbitol (70% Aqueous Solution) | q.s. 100% |

[1]Precipitated silica identified as Zeodent 119 offered by J. M. Huber

EXAMPLE IV

| Component | Weight % |
| --- | --- |
| $Na_2$ EDTA $2H_2O$ | 1.682 |
| Strontium Chloride $6H_2O$ | 1.200 |
| Sodium Fluoride | 0.443 |
| Silica Dental Abrasive[1] | 20.000 |
| Sodium Saccharin | 0.130 |
| Titanium Dioxide | 0.700 |
| Flavor | 0.600 |
| Carboxymethylcellulose | 0.600 |
| Sodium Alkyl Sulfate | 2.000 |
| Dye | 0.050 |
| Water | 19.000 |
| Sorbitol (70% Aqueous Solution) | q.s. 100% |

[1]Precipitated silica identified as Zeodent 119 offered by J. M. Huber

Fluoride Uptake Analysis

The ability of compositions of the present invention to deliver enhanced fluoride to dental enamel was measured using an in-vitro enamel disc method.

Enamel discs (4 mm diameter) were mounted in lucite rods, then ground and polished--removing at least 40 $\mu$m of the enamel surface. Discs were decalcified for 46 hours at 37° C. in 8 ml of 0.1M lactic acid plus $1.0 \times 10^{-4}$M disodium-methane-hydroxydiphosphonate (MHDP) adjusted to pH 4.5. The depth of demineralization was approximately 100 $\mu$m. The discs were placed in groups of four (4) per treatment group.

At the beginning of the study, each treatment group was suspended for one (1) hour in 15 grams of fresh, paraffin stimulated, pooled human saliva under constant agitation. The treatment groups were then exposed to 20 ml of an appropriate test solution for one (1) minute, followed by a thorough rinsing in deionized water. The one minute treatment was followed by one (1) hour soaking in the saliva baths. This cyclic pattern (one minute treatment/thorough rinse/one hour saliva soak) was repeated seven (7) times a day for four (4) days for a total of twenty-eight (28) treatments. Saliva baths were changed twice daily to maintain their freshness. At the end of each day, the discs were thoroughly rinsed with deionized water and placed upright in a moist atmosphere under refrigeration in order to minimize any microbial growth.

Following the 28th treatment, specimens were thoroughly rinsed with deionized water and analyzed for fluoride content using a microdrill biopsy technique. In this technique, a carbide dental bur (diameter approximately 0.45 mm) penetrates the surface of the discs and travels to the base of the demineralized area, in this case 100 $\mu$m. The displaced enamel powder is recovered into a small polyethylene vial, where it is dissolved with 20 $\mu$l of 0.5M $HClO_4$. To this is added 40 $\mu$l of deionized water, then 40 $\mu$l of a Citrate-EDTA buffer resulting in a total volume of 100 μl for analysis. Fluoride analysis of this solution is done using an Orion Fluoride Ion-specific electrode (Model 96-09-00) that has been appropriately calibrated for the range of these analytical samples.

Statistical analyses were done using a standard t- test for significance.

Using the above described procedure, various strontium ion concentrations were used with 1100 ppm F$^-$ to determine the amounts of F$^-$ taken up by the enamel.

| Treatment Solutions* | | |
|---|---|---|
| SR$^{++}$ (ppm) | F$^-$ (ppm) | F$^-$ Uptake (ug/cm$^2$) |
| 0 | 2200 | 20.9 ± 1.26 |
| 1100 | 1100 | 16.44 ± 3.23 |
| 2200 | 1100 | 16.05 ± 1.38 |
| 75 | 1100 | 15.55 ± 2.72 |
| 100 | 1100 | 15.47 ± 3.11 |
| 500 | 1100 | 14.10 ± 0.96 |
| 250 | 1100 | 13.98 ± 0.42 |
| 50 | 1100 | 13.93 ± 1.21 |
| 10 | 1100 | 13.57 ± 0.96 |
| 25 | 1100 | 13.52 ± 1.03 |
| 0 | 1100 | 10.07 ± 0.78 |

*Actual levels in test solutions were at ¼ these levels. These numbers represent the equivalents in whole dentifrice before dilution.
The numbers within the brackets are different from those outside at the 95% confidence level.

What is claimed is:

1. An oral composition effective against caries comprising:
   (a) an amount of a strontium disodium ethylenediamine tetraacetate, SrEDTA complex sufficient to provide from about 2 to about 900 ppm Sr$^{++}$;
   (b) an amount of a soluble fluoride ion source sufficient to provide from about 25 to about 50,000 ppm F$^-$; and
   (c) a pharmaceutically acceptable carrier.

2. An oral composition according to claim 1 in the form of a toothpaste containing a silica dental abrasive.

3. A method of applying fluoride ions to tooth enamel comprising applying to said enamel a safe and effective amount of a composition according to claim 1.

4. A method according to claim 3 wherein the composition contains sodium fluoride as the fluoride ion source.

* * * * *